(12) United States Patent
Enggaard et al.

(10) Patent No.: US 12,224,050 B2
(45) Date of Patent: Feb. 11, 2025

(54) CONTROL OF MEDICAL DEVICE USING WIRELESS COMMUNICATION

(71) Applicant: Novo Nordisk A/S, Bagsvaerd (DK)

(72) Inventors: Christian Peter Enggaard, Vejby (DK); Rune Ravn, Hasaselager (DK)

(73) Assignee: Novo Nordisk A/S., Bagsvaerd (DK)

( * ) Notice: Subject to any disclaimer, the term of this patent is extended or adjusted under 35 U.S.C. 154(b) by 499 days.

(21) Appl. No.: 16/760,026

(22) PCT Filed: Oct. 31, 2018

(86) PCT No.: PCT/EP2018/079847
§ 371 (c)(1),
(2) Date: Apr. 28, 2020

(87) PCT Pub. No.: WO2019/086527
PCT Pub. Date: May 9, 2019

(65) Prior Publication Data
US 2020/0294646 A1      Sep. 17, 2020

(30) Foreign Application Priority Data
Oct. 31, 2017   (EP) .................................... 17199399

(51) Int. Cl.
G16H 20/17      (2018.01)
A61M 5/315      (2006.01)
(Continued)

(52) U.S. Cl.
CPC ........ G16H 20/17 (2018.01); A61M 5/31535 (2013.01); A61M 5/31546 (2013.01);
(Continued)

(58) Field of Classification Search
CPC .................. G16H 40/67; G16H 20/17; A61M 2005/3125; A61M 5/31573; A61M 5/31546; A61M 5/3159
See application file for complete search history.

(56) References Cited

U.S. PATENT DOCUMENTS

| | | | |
|---|---|---|---|
| 6,010,492 A | 1/2000 | Jacobsen et al. | |
| 9,672,328 B2 | 6/2017 | Saint et al. | |

(Continued)

FOREIGN PATENT DOCUMENTS

| | | |
|---|---|---|
| CN | 102548467 A | 7/2012 |
| CN | 103874459 A | 6/2014 |

(Continued)

*Primary Examiner* — Tasnim Mehjabin Ahmed
(74) *Attorney, Agent, or Firm* — Wesley Nicolas

(57) ABSTRACT

The present invention provides a system (1) comprising: a pen injection device (10) holding a specific type of medicament and comprising a dose expelling mechanism and pen communication means (15), a mobile communication unit (30) comprising mobile communication means (35) adapted to communicate with the pen communication means (15), and a software application program configured to determine a recommended type of medicament to be delivered to a user based on information indicative of a physiological condition of the user, wherein the pen injection device (10) further comprises indication means which in a first state indicates that the dose expelling mechanism is to remain idle and in a second state indicates that the dose expelling mechanism is available for operation, and wherein the mobile communication unit (30) is configured to, via a communication from the mobile communication means (35) to the pen communication means (15), a) prompt a change of state of the indication means from the second state to the first state in response to the recommended type of medicament to be delivered differing from the specific type of medicament, and/or b) prompt a change of state of the indication means (Continued)

from the first state to the second state in response to the recommended type of medicament to be delivered corresponding to the specific type of medicament.

12 Claims, 1 Drawing Sheet

(51) Int. Cl.
  *G16H 40/67* (2018.01)
  *A61M 5/31* (2006.01)
(52) U.S. Cl.
  CPC .......... *A61M 5/3159* (2013.01); *G16H 40/67* (2018.01); *A61M 2005/3125* (2013.01); *A61M 5/31571* (2013.01); *A61M 5/31573* (2013.01); *A61M 2205/18* (2013.01); *A61M 2205/3553* (2013.01); *A61M 2205/50* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 10,252,002 | B2 | 4/2019 | Haider et al. |
| 10,391,235 | B2 | 8/2019 | Schabbach et al. |
| 2007/0078818 | A1 | 4/2007 | Zivitz et al. |
| 2008/0300534 | A1* | 12/2008 | Blomquist ............ G16H 40/67 604/66 |
| 2010/0016700 | A1 | 1/2010 | Sieh et al. |
| 2013/0245545 | A1 | 9/2013 | Arnold et al. |
| 2014/0324020 | A1 | 10/2014 | Stefansen |
| 2016/0012205 | A1* | 1/2016 | Saint ................. A61M 5/31528 604/189 |
| 2016/0030683 | A1 | 2/2016 | Taylor et al. |
| 2017/0098058 | A1 | 4/2017 | McCullough et al. |
| 2017/0106052 | A1 | 4/2017 | Spat et al. |
| 2017/0274149 | A1 | 9/2017 | Aeschlimann |
| 2017/0338864 | A1 | 11/2017 | Rolsted et al. |

FOREIGN PATENT DOCUMENTS

| | | |
|---|---|---|
| CN | 107073207 A | 8/2017 |
| CN | 107073213 A | 8/2017 |
| CN | 107106784 A | 8/2017 |
| EP | 3042676 A1 | 7/2016 |
| JP | 2007267870 A | 10/2007 |
| JP | 2013521963 A | 6/2013 |
| WO | 2010/098929 A1 | 9/2010 |
| WO | 2010/128493 A2 | 11/2010 |
| WO | 2015047870 A1 | 4/2015 |
| WO | 2016120207 | 8/2016 |

* cited by examiner

CONTROL OF MEDICAL DEVICE USING WIRELESS COMMUNICATION

CROSS-REFERENCE TO RELATED APPLICATIONS

This application is a 35 U.S.C. § 371 National Stage application of International Application PCT/EP2018/079847 (published as WO 2019/086527), filed Oct. 31, 2018, which claims priority to European Patent Application 17199399.1, filed Oct. 31, 2017; the contents of which are incorporated herein by reference.

FIELD OF THE INVENTION

The present invention relates generally to medical devices and more specifically to drug delivery devices, such as pen injectors, used for self-administration of a therapeutic substance.

BACKGROUND OF THE INVENTION

Some diseases entail a treatment regimen that involves administration of more than one type of medicament. For example, many people suffering from diabetes need to administer different types of insulin at different times of day in order to control their blood sugar level. A person with diabetes may administer a long-acting insulin once or twice a day and in addition thereto a short-acting insulin before meal-times and whenever necessary to avoid long-term hyperglycaemia.

In recent years, in an effort to optimise the individual treatment, mobile dose guidance software applications have been made available which provide various recommendations to a user, e.g. as to what type of insulin to take, at which point in time, etc., based on information transmitted from an injection pen and other input such as measured blood glucose. An example of such a dose guidance offering is the InPen solution from Companion Medical.

A dose guidance software application may for example recommend that a user administers a certain amount of long-acting insulin or a certain amount of short-acting insulin. However, many people with diabetes use insulins from the same manufacturer, which normally implies that the delivery is based on a manufacturer specific device platform. These insulins are therefore typically administered using injection pens of the same type having similar handling patterns. In fact, the injection pens often only distinguish from one another by having different colours or differently coloured labels. It is thus easy for, in particular, a new, busy or distracted user, to accidentally use the injection pen which contains the other type of insulin than the one recommended by the dose guidance software application. Even people using fairly different devices may confuse the one device for the other.

While a mix-up of drug products may be relatively harmless in some situations the effect of e.g. administering the wrong type of insulin can be fatal. It is thus desirable to provide a solution that eliminates, or at least markedly reduces, the risk of inadvertently administering the wrong type of medicament.

SUMMARY OF THE INVENTION

It is an object of the invention to eliminate or reduce at least one drawback of the prior art, or to provide a useful alternative to prior art solutions.

In particular, it is an object of the invention to provide a solution for a decision support system which reduces the risk of a user inadvertently administering a type of medicament which differs from a recommended type of medicament.

It is a further object of the invention to provide a solution which reduces the risk of a user inadvertently mixing up two injection devices containing different types of medicament.

In the disclosure of the present invention, aspects and embodiments will be described which will address one or more of the above objects and/or which will address objects apparent from the following text.

In one aspect the invention provides a system according to claim 1.

Accordingly, a system is provided comprising:
a pen injection device holding a specific type of medicament and comprising a dose expelling mechanism and pen communication means,
a mobile communication unit comprising mobile communication means adapted to communicate with the pen communication means, and
a software application program configured to determine a recommended type of medicament to be delivered to a user based on information indicative of a physiological condition of the user, and to compare the recommended type of medicament with the specific type of medicament.

The pen injection device further comprises indication means which in a first state, e.g. an active state, indicates that the dose expelling mechanism is to remain idle and in a second state, e.g. an inactive state, indicates that the dose expelling mechanism is available for operation.

The mobile communication unit is configured to, via a communication from the mobile communication means to the pen communication means, a) if the indication means is in the second state prompt a change of state of the indication means from the second state to the first state in response to the software application program identifying that the recommended type of medicament to be delivered differs from the specific type of medicament, and/or b) if the indication means is in the first state prompt a change of state of the indication means from the first state to the second state in response to the software application program identifying that the recommended type of medicament to be delivered corresponds to the specific type of medicament.

Hence, the mobile communication unit controls the pen injection device based on dose guidance input from the software application program and commands the pen injection device to provide an indication whether it is to be used or not depending on the specific dose guidance. In case the indication means is by default in the second state the mobile communication unit is configured to change the state of the indication means to reflect that the dose expelling mechanism is to remain idle, i.e. that the pen injection device is not to be used, in response to the software application program recommending administration of a medicament which is different from the specific type of medicament, and/or in case the indication means is by default in the first state the mobile communication unit is configured to change the state of the indication means to reflect that the dose expelling mechanism is available for operation, i.e. that the pen injection device is to be used, in response to the software application program recommending administration of a medicament which corresponds to the specific type of medicament.

Such a system eliminates, or at least markedly reduces, the risk of a user inadvertently administering the specific type of medicament when the recommended type of medicament to be delivered differs therefrom.

In case the indication means is in the second state and the recommended type of medicament to be delivered corresponds to the specific type of medicament the second state of the indication means may remain unchanged, or the mobile communication unit may alternatively further be configured to prompt a highlighting of the second state.

For a system where the indication means is always by default, for example, in the second state the mobile communication unit may simply only be configured to carry out a).

The recommended type of medicament may be selected from a group consisting of a) a first type of diabetes medication and b) a second type of diabetes medication. In exemplary embodiments of the invention the recommended type of medicament is selected from a group consisting of a) a rapid acting insulin and b) a long acting insulin, The software application program, which may be stored in a memory of a data processor in the mobile communication unit or associated with a communication network accessible via the Internet and wirelessly linked with the mobile communication unit, may be configured to determine the recommended type of medicament to be delivered based at least in part on information sent from the pen communication means to the mobile communication means.

This allows for a transfer of e.g. dose history data to the mobile communication unit, i.a. informing about the time of last use of the pen injection device.

The software application program may further be configured to determine the recommended type of medicament to be delivered based on information about a current and/or trending glucose level of the user. Such information may be retrieved from a glucose monitoring device.

The pen injection device may further comprise a dose setting mechanism operable to set a dose to be delivered, and prompting a change of state of the indication means from the second state to the first state may comprise disabling the dose setting mechanism. For example, a solenoid in the pen injection device may be activated responsive to a control signal from the mobile communication means to cause a pawl to engage with the dose setting mechanism, e.g. a dose dial member, thereby mechanically preventing operations thereof. This will effectively prevent a user from setting a dose and thereby from delivering any dose of the specific type of medicament.

Alternatively, or additionally, the indication means may comprise a dose display for visual confirmation of a set dose, and prompting a change of state of the indication means from the second state to the first state may comprise affecting the dose display. This will notify the user immediately when she for example tries to set a dose to be delivered by operating the dose dial member.

If, for example, the dose display comprises an electronic display prompting a change of state of the indication means from the second state to the first state may comprise switching off, freezing or otherwise manipulating a visual state of the electronic display.

Alternatively, if the dose display comprises a mechanical display, e.g. including a dose indicia carrying scale drum partially visible through a window in a housing of the pen injection device, and the window is covered by switchable glass, prompting a change of state of the indication means from the second state to the first state may comprise applying a voltage to the switchable glass to increase the opacity thereof.

Prompting a change of state of the indication means from the second state to the first state may alternatively, or additionally, comprise disabling the dose expelling mechanism. This could e.g. be realised by use of a solenoid arrangement similarly to the above described arrangement for disabling the dose setting mechanism, only where the pawl is displaceable to engage with the dose expelling mechanism, e.g. a piston actuator member.

The indication means may alternatively, or additionally, comprise a sound generator, and prompting a change of state of the indication means from the second state to the first state may comprise producing a notifying sound, thereby audibly alerting the user that the pen injection device is not to be used.

The indication means may alternatively, or additionally, comprise a vibrator device, and prompting a change of state of the indication means from the second state to the first state may comprise producing a tactile warning signal.

Prompting a change of state of the indication means from the first state to the second state may comprise providing a visual, audible and/or tactile signal that use of the pen injection device is recommended.

The mobile communication unit may further comprise an alert generator adapted emit an alert signal. The pen communication means may be configured to register and to notify the mobile communication means in case the dose expelling mechanism and/or the dose setting mechanism is being operated, and the alert generator may configured to emit the alert signal if the mobile communication means receives a notification from the pen communication means (that the dose expelling mechanism or the dose setting mechanism is being operated) and the recommended type of medicament differs from the specific type of medicament.

In that case the mobile communication unit alerts the user if she operates the pen injection device despite the indication means indicating that the dose expelling mechanism is to remain idle.

The mobile communication means may e.g. be adapted to communicate with the pen injection device via Bluetooth or near field communication (NFC) protocols and the mobile communication unit may thus be able to affect the indication means as long as the pen injection device is within the communication radius of the mobile communication unit.

It is further envisioned that the system may be configured to prevent operation of the pen injection device, e.g. to prevent dose setting and/or dose expelling, if the pen injection device is outside the communication radius of the mobile communication unit.

In another aspect of the invention a system is provided comprising:
  a first pen injection device holding a first specific type of medicament and comprising a first dose expelling mechanism and first pen communication means,
  a second pen injection device holding a second specific type of medicament and comprising a second dose expelling mechanism and second pen communication means,
  a mobile communication unit comprising mobile communication means adapted to communicate with the first pen communication means and the second pen communication means, and
  a software application program being configured to determine a recommended type of medicament to be delivered to a user as one of the first specific type of medicament and the second specific type of medicament based on information indicative of a physiological condition of the user, wherein the first pen injection device further comprises first indication means which when active indicates that the first dose expelling mechanism is to remain idle and when inactive indicates that the first dose expelling mechanism is available for operation, and the second pen injection device further comprises second indication means which when active indicates that the second dose expelling mechanism is to remain idle and when inactive indicates that the second dose expelling mechanism is available for operation, and wherein the mobile communication unit is configured to, via a communication from the mobile communication means to at least one of the first pen communication means and the second pen communication means, a) prompt an activation of an inactive first indication means and/or a deactivation of an active second indication means in response to the recommended type of medicament to be delivered being the second specific type of medicament, and b) prompt an activation of an inactive second indication means and/or a deactivation of an active first indication means in response to the recommended type of medicament to be delivered being the first specific type of medicament.

Thereby, a dosing system of two pen injection devices carrying different types of drug, e.g. long acting insulin, respectively rapid acting insulin, may be controlled by the mobile communication unit to clearly indicate to the user which of them is to be used for an impending injection, eliminating, or at least markedly reducing, the risk of the user inadvertently injecting the type of drug which is not presently recommended.

Each of the first indication means and the second indication means may by default be active or inactive, i.e. they may both be inactive, both be active, or one may be active while the other may be inactive. It can also be contemplated that one or both of the first indication means and the second indication means may change a default setting during use of the system, e.g. following the communication from the mobile communication means, such that for example a by default inactive first indication means changes to a by default active first indication means following a recommendation from the software application program to deliver the second specific type of medicament.

Hence, for example, if the first pen injection device is not to be used the system may emphasize that it is not to be used by prompting an activation of the first indication means, e.g. by changing the visual state of a display, or, in case the first indication means is by default active, simply maintain the active state. Alternatively, if the first pen injection device is to be used the system may highlight that it is to be used, e.g. by lighting up an electronic display, or, in case the first indication means is by default inactive, simply maintain the inactive state.

In a further aspect of the invention a system is provided comprising:
a pen injection device holding a specific type of medicament and comprising a dose expelling mechanism and pen communication means,
a mobile communication unit comprising mobile communication means adapted to communicate with the pen communication means,
a software application program configured to determine a recommended type of medicament to be delivered to a user based on information indicative of a physiological condition of the user, and to compare the recommended type of medicament with the specific type of medicament, and
an alert generator communicatively connected with the software application program and configured to register an operation of the dose expelling mechanism and to emit an alert signal in response to registering an operation of the dose expelling mechanism when the recommended type of medicament differs from the specific type of medicament.

Thereby, a system is provided which signals to the user that she is expelling a type of medicament which differs from a recommended type of medicament, allowing her to either carry on with the knowledge that a different type of medicament is being administered or to interrupt the dose expelling and perform any remedial actions.

In a further aspect of the invention a system is provided comprising:
a pen injection device holding a specific type of medicament and comprising a dose setting mechanism operable to set a dose of the specific type of medicament to be expelled, a dose expelling mechanism and pen communication means,
a mobile communication unit comprising mobile communication means adapted to communicate with the pen communication means,
a software application program configured to determine a recommended type of medicament to be delivered to a user based on information indicative of a physiological condition of the user, and to compare the recommended type of medicament with the specific type of medicament, and
an alert generator communicatively connected with the software application program and configured to register an operation of the dose setting mechanism and to emit an alert signal in response to registering an operation of the dose setting mechanism when the recommended type of medicament differs from the specific type of medicament.

Thereby, a system is provided which alerts the user already during setting of a dose that she is preparing to inject herself with a different type of medication than the one recommended. The user can thereby change her course of action in due time before needing to perform any remedial actions.

The alert generator may be incorporated in the pen injection device, in the mobile communication unit, or in a third device communicatively connected with the pen communication means, and the alert signal may be an audible, visible, and/or tactile signal.

In case the alert generator forms part of the mobile communication unit the alert generator may be configured to register an operation of the dose expelling mechanism or an operation of the dose setting mechanism by the pen communication means registering the operation of the dose expelling mechanism or the operation of the dose setting mechanism, e.g. via one or more intermediate components, and notifying the mobile communication means in response.

In a further aspect of the invention a system is provided comprising:
a first pen injection device holding a first specific type of medicament and comprising a first dose expelling mechanism and first pen communication means,
a second pen injection device holding a second specific type of medicament and comprising a second dose expelling mechanism and second pen communication means,
a mobile communication unit comprising mobile communication means adapted to communicate with the first pen communication means and the second pen communication means, and an alert generator adapted to emit an alert signal, and a software application program configured to determine a recommended type of medicament to be delivered to a user as one of the first specific type of medicament and the second specific type of medicament based on information indicative of a physiological condition of the user, wherein the first pen communication means is configured to register an operation of the first dose expelling mechanism and to notify the mobile communication means in response to the first dose expelling mechanism being operated, and the second pen communication means is configured to register an operation of the second dose expelling mechanism and to notify the mobile communication means in response to the second dose expelling mechanism being operated, and wherein the alert generator is configured to emit the alert signal in response to the mobile communication means receiving a notification from the first pen communication means when the recommended type of medicament is the second specific type of medicament, and in response to the mobile communication means receiving a notification from the second pen communication means when the recommended type of medicament is the first specific type of medicament.

Such a system will alert a user who treats herself with different types of drugs from different injection devices in case she accidentally sets out to inject herself with the other type of medicament than the one recommended. For example, if the user suffers from insulin dependent diabetes mellitus and regularly administers both a rapid acting and a long acting insulin the system will provide an alert if e.g. the software application program recommends a dose of the rapid acting insulin and she starts to expel the, or a, dose of the long acting insulin.

In a further aspect of the invention a system is provided comprising:
  a first pen injection device holding a first specific type of medicament and comprising a first dose setting mechanism operable to set a dose of the first specific type of medicament to be expelled, a first dose expelling mechanism and first pen communication means,
  a second pen injection device holding a second specific type of medicament and comprising a second dose setting mechanism operable to set a dose of the second specific type of medicament to be expelled, a second dose expelling mechanism and second pen communication means,
  a mobile communication unit comprising mobile communication means adapted to communicate with the first pen communication means and the second pen communication means, and an alert generator adapted to emit an alert signal, and
  a software application program configured to determine a recommended type of medicament to be delivered to a user as one of the first specific type of medicament and the second specific type of medicament based on information indicative of a physiological condition of the user, wherein the first pen communication means is configured to register an operation of the first dose setting mechanism and to notify the mobile communication means in response to the first dose setting mechanism being operated, and the second pen communication means is configured to register an operation of the second dose setting mechanism and to notify the mobile communication means in response to the second dose setting mechanism being operated, and wherein the alert generator is configured to emit the alert signal in response to the mobile communication means receiving a notification from the first pen communication means when the recommended type of medicament is the second specific type of medicament, and in response to the mobile communication means receiving a notification from the second pen communication means when the recommended type of medicament is the first specific type of medicament.

Such a system will alert a user who treats herself with different types of drugs from different injection devices in case she accidentally prepares to inject herself with the other type of medicament than the one recommended by performing a dose setting operation on the pen injection device which holds the type of medicament that is not to be used. The user can thereby in due time change to the pen injection device which holds the recommended type of medicament, avoiding a potentially dangerous mix-up.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

The shown figures are schematic representations for which reason the configuration of the different structures as well as their relative dimensions are intended to serve illustrative purposes only.

Figure 1:
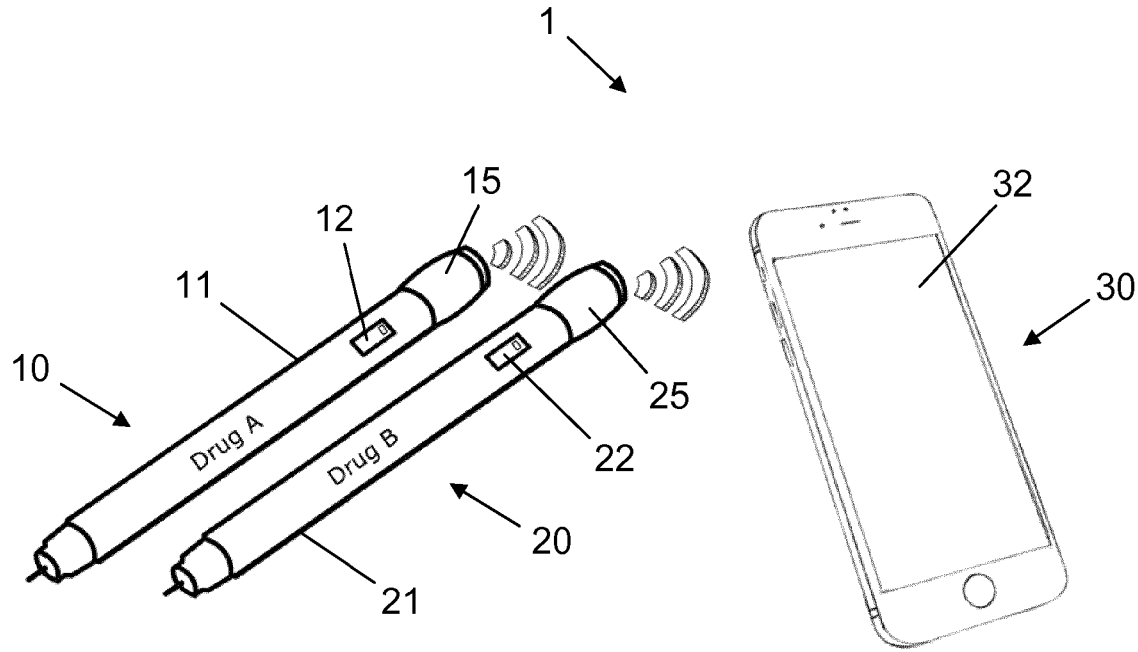
FIG. 1 illustrates a system according to an embodiment of the invention comprising two injection devices and a smartphone during data collection before providing dose guidance.

FIG. 1 shows a system 1 according to an exemplary embodiment of the invention. The system 1 comprises a first injection pen 10 holding a first medicament, "Drug A", a second injection pen 20 holding a second medicament, "Drug B", and a smartphone 30 adapted for bidirectional communication with each of the two injection pens 10, 20.

The first injection pen 10 has a first housing 11 which accommodates a first dose setting mechanism (not visible) and a first injection mechanism (not visible), and a first electronic display 12 adapted to show the size of a currently set dose to be delivered by the first injection mechanism. Furthermore, a first transceiver 15 is arranged at a proximal end portion of the first housing 11 for communication with the smartphone 30.

Similarly, the second injection pen 20 has a second housing 21 which accommodates a second dose setting mechanism (not visible) and a second injection mechanism (not visible), and a second electronic display 22 adapted to show the size of a currently set dose to be delivered by the second injection mechanism. Furthermore, a second transceiver 25 is arranged at a proximal end portion of the second housing 21 for communication with the smartphone 30.

The smartphone 30 has a touch sensitive screen 32 which functions as an input/output interface, and includes a software application program, or app, which is configured to provide dose guidance to a user of the system 1 on the basis of previous use information from the two injection pens 10, 20 as well as other relevant information such as e.g. a determined blood glucose level and/or a predefined dosing schedule. Furthermore, the smartphone 30 has a smartphone transceiver 35 for respective communication with the first transceiver 15 and the second transceiver 25, and an alert generator in the form of a speaker 38.

In FIG. 1 the first transceiver 15 transmits first dose history data, e.g. comprising time of last use and last ejected dose of "Drug A", while the second transceiver 25 transmits second dose history data, e.g. comprising time of last use and last ejected dose of "Drug B", to the smartphone 30 prior to the dose guidance provision. At this point the first electronic display 12 shows the numeral '0', indicating that the first injection device 10 is ready for a dose setting operation, and the second electronic display 22 also shows the numeral '0', indicating that the second injection device 20 is ready for a dose setting operation.

Figure 2:
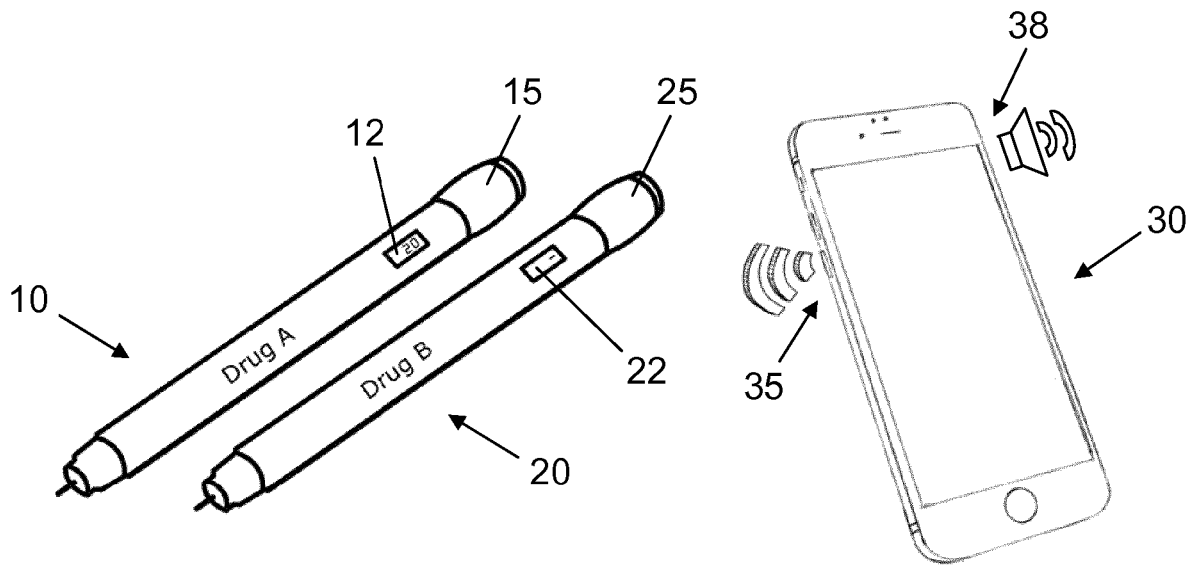
FIG. 2 illustrates the system after dose guidance is provided.

FIG. 2 shows the system 1 after the dose guidance provision and illustrates a control transmission being made from the smartphone 30 to the two injection pens 10, 20. In the present example the app has recommended an administration of 20 units of "Drug A" and the control transmission accordingly includes a control signal to the second transceiver 25 dictating a blanking out of the second electronic display 22. Thereby, the second electronic display 22 provides a clear visual indication to the user that the second injection pen 20 is not to be used in connection with the impending dose administration.

In case the first injection pen 10 is an electronically operated device the control transmission may further include a control signal to the first transceiver 15 dictating an automatic setting of a dose of 20 units, as indicated in FIG. 2. However, if the first injection pen 10 is a mechanically operated device the control signal may instead dictate a lighting up of the first electronic display 12, signalling to the user that this is the pen to be used, or the control transmission may simply only be directed at the second injection pen 20, leaving the '0' in the first electronic display.

Should the user pick up the second injection pen 20 and begin to operate the second dose setting mechanism anyway to thereby prepare for an injection of "Drug B" a sensor (not visible) in the second housing 21 will register the dose setting action, e.g. by noticing a relative movement of two components associated with the second dose setting mechanism, and the second transceiver 25 will accordingly transmit a notification to the smartphone transceiver 35. Upon receiving this notification the smartphone 30 will issue an alert via the speaker 38 as an additional indication of the recommended drug type, serving as a warning to the user that a mistake is about to be made.

The invention claimed is:

1. A pen injection safety system having two-way communication between a mobile communication unit and at least two pen injection devices, the system comprising:
   a first pen injection device holding a first specific type of medicament and comprising:
      a first dose expelling mechanism,
      a first pen communication structure, and
      a first indication structure which in a first state indicates that the first dose expelling mechanism is to remain idle and in a second state indicates that the first dose expelling mechanism is available for operation,
   a second pen injection device holding a second specific type of medicament and comprising:
      a second dose expelling mechanism,
      a second pen communication structure, and
      a second indication structure which in a first state indicates that the second dose expelling mechanism is to remain idle and in a second state indicates that the second dose expelling mechanism is available for operation,
   the mobile communication unit comprising mobile communication structure adapted for two-way communication with each of the first pen communication structure and the second pen communication structure, and
   a software application program configured to determine a recommended type of medicament to be delivered to a user as one of the first specific type of medicament and the second specific type of medicament based on information indicative of a physiological condition of the user,
wherein the mobile communication unit is configured to, via a communication from the mobile communication structure to at least one of the first pen communication structure and the second pen communication structure,
   prompt a change of state of the first indication structure from the second state to the first state and/or a change of state of the second indication structure from the first state to the second state in response to the recommended type of medicament to be delivered being the second specific type of medicament, and
   prompt a change of state of the second indication structure from the second state to the first state and/or a change of state of the first indication structure from the first state to the second state in response to the recommended type of medicament to be delivered being the first specific type of medicament,
thereby providing a pen injection safety system reducing the risk of the user inadvertently administering medicament which differs from the recommended type of medicament.

2. The pen injection safety system according to claim 1, wherein the software application program is configured to determine the recommended type of medicament to be delivered based at least in part on information sent from the first pen communication structure to the mobile communication structure.

3. The pen injection safety system according to claim 1, wherein the first pen injection device further comprises a dose setting mechanism operable to set a dose to be delivered.

4. The pen injection safety system according to claim 3, wherein prompting a change of state of the first indication structure from the second state to the first state comprises disabling the dose setting mechanism.

5. The pen injection safety system according to claim 3, wherein the first pen injection device further comprises a dose display for visual confirmation of a set dose, and wherein prompting the change of state of the first indication structure from the second state to the first state comprises affecting the dose display.

6. The pen injection safety system according to claim 3, wherein the mobile communication unit further comprises an alert generator adapted emit an alert signal, wherein the first pen communication structure is configured to register and to notify the mobile communication structure of an ongoing operation of the dose setting mechanism, and wherein the alert generator is configured to emit the alert signal, if the mobile communication structure receives a notification from the first pen communication structure and the recommended type of medicament is the second specific type of medicament.

7. The pen injection safety system according to claim 1, wherein the first pen injection device further comprises a sound generator, and wherein prompting the change of state of the first indication structure from the second state to the first state comprises producing a notifying sound via the sound generator.

8. The pen injection safety system according to claim 1, wherein prompting the change of state of the first indication structure from the second state to the first state comprises disabling the first dose expelling mechanism.

9. The pen injection safety system according to claim 1, wherein the mobile communication unit further comprises an alert generator adapted emit an alert signal, wherein the first pen communication structure is configured to register and to notify the mobile communication structure of an ongoing operation of the first dose expelling mechanism, and wherein the alert generator is configured to emit the alert signal, if the mobile communication structure receives a notification from the first pen communication structure and the recommended type of medicament is the second specific type of medicament.

10. The pen injection safety system according to claim 1, wherein the recommended type of medicament is selected from a group consisting of a) a first type of diabetes medication and b) a second type of diabetes medication.

11. The pen injection safety system according to claim 10, wherein the first type of diabetes medication is a rapid acting insulin and the second type of diabetes medication is a long acting insulin.

12. The pen injection safety system according to claim 1, wherein prompting a change of state of the first indication structure from the first state to the second state comprises providing a visual, audible and/or tactile signal that the first pen injection device is ready to be used.

* * * * *

UNITED STATES PATENT AND TRADEMARK OFFICE
CERTIFICATE OF CORRECTION

| | | |
|---|---|---|
| PATENT NO. | : 12,224,050 B2 | Page 1 of 1 |
| APPLICATION NO. | : 16/760026 | |
| DATED | : February 11, 2025 | |
| INVENTOR(S) | : Christian Peter Enggaard et al. | |

It is certified that error appears in the above-identified patent and that said Letters Patent is hereby corrected as shown below:

On the Title Page

At Column 1, Item (72) Inventors Address, Please delete "Hasaselager" and insert --Hasselager--

Signed and Sealed this
Fourteenth Day of October, 2025

John A. Squires
*Director of the United States Patent and Trademark Office*